United States Patent [19]

Hodge et al.

[11] Patent Number: 4,973,418

[45] Date of Patent: Nov. 27, 1990

[54] NITROGEN-CONTAINING ANHYDRIDES AS BLEACH ACTIVATORS IN DETERGENT COMPOSITIONS

[75] Inventors: Stephen R. Hodge, Kirkella; Andrew Pearce, Brough, both of England

[73] Assignee: BP Chemicals Limited, London, England

[21] Appl. No.: 401,444

[22] PCT Filed: Feb. 9, 1989

[86] PCT No.: PCT/GB89/00131

§ 371 Date: Sep. 13, 1989

§ 102(e) Date: Sep. 13, 1989

[87] PCT Pub. No.: WO89/07640

PCT Pub. Date: Aug. 24, 1989

[30] Foreign Application Priority Data

Feb. 11, 1988 [GB] United Kingdom ............... 8803113

[51] Int. Cl.$^5$ ................ C11D 3/39; C11D 3/28
[52] U.S. Cl. ................... 252/102; 252/95; 252/99; 252/186.4; 252/186.41
[58] Field of Search ............. 252/95, 99, 102, 186.4, 252/186.41

[56] References Cited

U.S. PATENT DOCUMENTS

| | | | |
|---|---|---|---|
| 3,775,333 | 11/1973 | Loffelman et al. | 252/99 |
| 3,840,466 | 10/1974 | Gray | 252/99 |
| 3,850,920 | 11/1974 | Walles | 252/102 |
| 3,928,223 | 12/1975 | Murray | 252/95 |
| 4,147,654 | 4/1979 | Rapko | 252/186.4 |
| 4,271,031 | 6/1981 | Oppenlaender et al. | 252/95 |
| 4,551,263 | 11/1985 | Schellhammer et al. | 252/102 |

*Primary Examiner*—Prince E. Willis
*Attorney, Agent, or Firm*—Brooks Haidt Haffner & Delahunty

[57] ABSTRACT

The present invention relates to a detergent composition in aqueous solution comprising,
(i) a surfactant selected from anionic, nonionic, zwitterionic and cationic surfactants and mixtures thereof,
(ii) a precursor compound capable of giving rise to a peroxygen compound in the presence of water,
(iii) a bleach activator capable of enhancing the bleaching activity of the peroxygen compound so formed,
(iv) a suds suppressing agent and
(v) a detergent builder, characterized in that the bleach activator comprises one or more cyclic anhydrides containing at least one nitrogen atom in the alpha position with respect to at least one of the carbonyl functions in the anhydride and the activator is at least partially soluble in water.

These compounds show bleaching activity at relatively low temperatures.

14 Claims, No Drawings

NITROGEN-CONTAINING ANHYDRIDES AS BLEACH ACTIVATORS IN DETERGENT COMPOSITIONS

The present invention relates to the use of anhydrides as bleach activators, especially in detergent compositions.

Compounds such as tetraacetyl ethylene diamine (hereafter referred to as "TAED") are well known. Processes for the production of such compounds are disclosed for instance in published German patent application No. 2832021. These compounds are said to be efficient in activating the conventional inorganic salts used as bleach precursors in detergent compositions and generate peracetic acid in situ by the reaction thereof with alkaline hydrogen peroxide. The activating agent for the bleach precursor is the so-called bleach activator. Specific examples of such bleach precursors are sodium perborate and sodium percarbonate. In the absence of the activators the bleach precursor is satisfactorily effective only at elevated temperatures, its effectiveness being very slow at lower temperatures. The use of compounds such as TAED enable the bleach precursor to function more effectively at temperatures of the order of 60° C.

It has now been found that certain anhydrides function as efficient additives in activating the bleach precursor in detergent compositions, especially at low temperatures.

Accordingly the present invention is a detergent composition in aqueous solution comprising (i) a surfactant selected from anionic, nonionic, zwitterionic and cationic surfactants and mixtures thereof, (ii) a precursor compound capable of giving rise to a peroxygen compound in the presence of water, (iii) a bleach activator capable of enhancing the bleaching activity of the peroxygen compound so formed, (iv) a suds suppressing agent and (v) a detergent builder, characterised in that the bleach activator comprises one or more cyclic anhydrides containing at least one nitrogen atom in the alpha position with respect to at least one of the carbonyl functions in the anhydride and the activator is at least partially soluble in water.

Thus such compounds may be represented by the generic formula

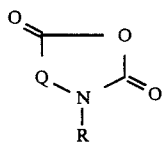

(I)

wherein Q is a divalent organic grouping such that Q and N together with the carbonyl and oxygen functions in the anhydride group form one or more cyclic structures, and R is H, an alkyl, aryl, halogen, a carboxylic or a carbonyl containing function.

Where R has an aryl, alkaryl or aralkyl containing functions, it is essential that such functions also carry a substituent capable of solubilising the activator in aqueous systems e.g. a sulphonic acid group. Where R is a halogen containing functions, the halogen is preferably chlorine or bromine.

An example of such compound is that shown in formula (II) below:

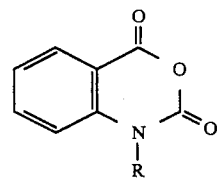

(II)

In the formula (II) above, where R=H; isatoic anhydride or 2H-3,1-Benzoxazine-2,4-(1H)dione [Chem. Reg. No. 118-48-91] R=Me; N-methyl Isatoic anhydride or 2H-3,1-Benzoxazine-2,4-(1H)dione 1-methyl [Chem. Reg. No. 10328-92-4]. Another compound of this type is a compound of formula (III) below:

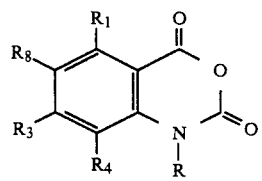

(III)

wherein R has the same significance as in formula (I) above, and $R_1$, $R_2$, $R_3$ and $R_4$ may be the same or different nuclear substituents and may be selected from H, halogen, alkyl, alkenyl, aryl, alkoxyl, amino, $COOR_5$, (where $R_5$ is an H or an alkyl group) and carbonyl containing functions. Specific examples of such compounds include cases where:

(a) $R=R_1=R_4=H$ and $R_2=R_3=OCH_3$
(b) $R=R_1=R_2=R_3=H$ and $R_4=CH_3$
(c) $R=R_1=R_3=R_4=H$ and $R_2=CH_3$
(d) $R=R_2=R_3=R_4=H$ and $R_1=CH_3$
(e) $R=R_1=R_3=R_4=H$ and $R_2=Cl$ or Br
(f) $R=R_1=R_2=R_4=H$ and $R_3=Cl$ or $CO_2H$ or $NO_2$, or
(g) $R_1=R_2=R_3=R_4=H$ and $R=CH_3CO$. or Cl A further compound of this type is shown in formula (IV) below:

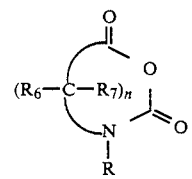

(IV)

where R has the same significance as in formula (I) above, and $R_6$ and $R_7$ may be the same or different groups and may be any one of the groups listed in the context of $R_1$ to $R_4$ above and n has a value from 1-3. Another compound falling within formula (I) can be represented by (V)

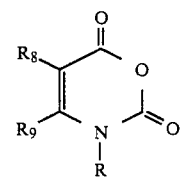

(V)

wherein R has the same significance as in formula (I) above, and $R_8$ and $R_9$ are the same or different groups and may be any one of the groups designated for the substituents $R_1-R_4$ above except that both $R_8$ and $R_9$ should not be H, or which together form one or more cyclic structure with or without additional hetero atoms. One example of such a compound in where $R_8$ and $R_9$ together represent one or more benzene rings as in formula (III) above, or, where they together with the hydrocarbyl carbon atoms in the anhydride ring represent a pyridine, pyrazole, pyrimidine or an imidazole ring.

Compounds of structure (V) can be synthesised by the reaction of trimethyl silylazide with the corresponding anhydride. The reaction involves a Hofmann rearrangement of the intermediate acyl azide.

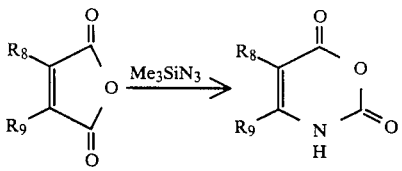

A further example of such a compound is that represented by formula (VI) below:

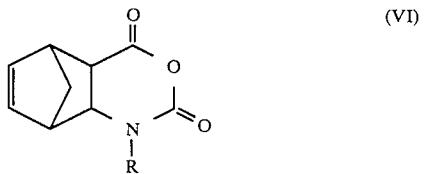

(VI)

wherein R has the same significance as in formula (I) above.

The bleach activator is at least partially soluble in water. Thus the solubility is at least 0.01% w/w in water at ambient temperature, e.g. 25° C.

It is believed that the activators of the present invention preferentially react with the peroxygen compound, e.g. hydrogen peroxide generated by contacting the precursor compound with water. This is believed to result in a peroxygen species of enhanced bleaching activity than that initially generated.

The bleach activators of the present invention can be used or in conjunction with other conventional activators such as TAED, phthalic anhydride, maleic anhydride, succinic anhydride isononanoyl oxybenzene sulphonate (also known as isonobs') and tetracetyl glycoluril (also known as "TAGU") and the like or with mixtures of such known activators.

Any of the well known surfactants can be used in the detergent compositions of the present invention. A typical list of these surfactants can be found in EP No. 0120591 and in U.S. Pat. No. 3,663,961.

Examples of water soluble anionic surfactants include the salts of alkyl benzene sulphonates, paraffin sulphonates, alpha-olefin sulphonates, alkyl glyceryl ether sulphonates and 2-acyloxy alkane-1-sulphonate, and beta-alkyloxy alkane sulphonate. Similarly, salts of alkyl sulphates, alkyl polyalkoxy ether sulphates, alpha-sulpho-carboxylates and their esters, fatty acid monoglyceride sulphates and sulphonates and alkyl phenol polyalkoxy ether sulphates may also be used.

Suitable examples of the above surfactants are linear straight chain alkyl benzene sulphonates having alkyl groups with 8-16 carbon atoms and methyl branched alkyl sulphates having 8-16 carbon atoms which are also effective.

Other anionic detergent compounds suitable for use herein include the sodium alkyl glyceryl ether sulphonates derived from tallow and coconut oil; sodium fatty acid monoglyceride sulphonates and sulphates derived from coconut oil; and sodium or potassium salts of $C_8-C_{12}$ alkyl phenol alkylene oxide ether sulphate containing up to 10 alkylene oxide units per molecule. Mixtures of anionic surfactants may also be used.

A substantial list of such compounds can be found in e.g. McCutcheon's Dictionary of Emulsifiers and Detergents, International Edition (1981), published by the Manufacturing Confectioner Publishing Co. and in "Surfactants Europa: A Directory of Surface Active Agents available in Europe", Ed. Gordon L. Hollis, Vol 1 (1982), published by George Goodwin.

The nonionic surfactants which may be used in the present invention are condensates of an alkylene oxide e.g. ethylene oxide with a hydrophobic group to form a surfactant having an appropriate hydrophilic-lipophilic balance (HLB) in the range from 8 to 17, suitably from 9.5 to 13.5, preferably from 10 to 12.5. The hydrophobic group may be an aliphatic or aromatic type and the length of the polyoxyethylene group condensed therewith can be readily adjusted to yield a water-soluble compound having the desired degree of HLB.

Examples of suitable nonionic surfactants include:

(a) The polyethylene oxide condensates of alkyl phenol in which the alkyl group e.g. contains from 6 to 12 carbon atoms and in which from 3 to 30 moles, preferably 5 to 14 moles of ethylene oxide are present. Other examples include a mole of dodecylphenol condensed with 9 moles of ethylene oxide, a mole of dinonylphenol condensed with 11 moles of ethylene oxide and a mole of nonylphenol and octadecylphenol condensed with 13 moles of ethylene oxide.

(a) The nonionic surfactant may also be formed as a condensation product of a mole of primary or secondary $C_8-C_{24}$ aliphatic alcohols with from 2 to 40 moles, preferably 2 to 9 moles of ethylene oxide.

Specific examples of nonionic surfactants useful for the purposes of the invention include the various grades of Dobanol (Registered Trade Mark, supplied by Shell) Lutensol (Registered Trade Mark, supplied by BASF) and Synperonics (Registered Trade Mark, supplied by ICI).

Other useful nonionic surfactants include the synthetic nonionic detergents available on the market under "Pluronics" (Registered Trade Mark) and supplied by Wyandotte Chemicals Corporation.

Zwitterionic compounds such as betaines and sulphobetaines, particularly those with a $C_8-C_{16}$ alkyl substituent on the nitrogen atom can also be used as surfactants.

Examples of cationic surfactants that can be used include e.g. quaternary ammonium surfactants and surfactants of a semi-polar nature, for example amine oxides. Suitable quaternary ammonium surfactants are the mono $C_8-C_{16}$, N-alkyl or alkenyl ammonium surfactants in which remaining N valences are methyl, hydroxyethyl or hydroxypropyl groups. Suitable examples of amine oxides are the mono $C_8-C_{20}$, N-alkyl or alkenyl amine oxides and the propylene-1,3-diamine dioxides in which the remaining N valences are methyl, hydroxyethyl or hydroxypropyl substituents.

The detergent compositions can comprise from 1 to 70% w/w, suitably from 1 to 20% w/w of the total composition. Mixtures of anionic with nonionic or zwitterionic surfactant types are preferred.

Suitable bleach precursors which act as a source of a peroxygen compound e.g. hydrogen peroxide include sodium perborate mono and tetrahydrate, sodium percarbonate, sodium persilicate and the clathrate $4Na_2SO_4:2H_2O_2:1\ NaCl$.

If clathrate materials are used as peroxygen source (bleach precursor), a separate source of alkalinity will be required and for stability reasons these are preferably stored separately from the hydrogen peroxide source. The precursor compound (ii) acting as the hydrogen peroxide source can be present in an amount of from 1 to 40% w/w suitably from 5 to 35% by weight, preferably from 10 to 30% by weight of the total composition.

In the detergent compositions of the present invention the molar ratio of peroxygen compound e.g. hydrogen peroxide generated from a bleach precursor to bleach activator is suitably greater than 1.5:1, preferably at least 2.0. Under the usage conditions encountered in domestic laundry practice, the molar ratio of bleach precursor to bleach activator is generally greater than 5.0:1 and is most preferably greater than 10:1.

Suds suppressing agents which are useful in the detergent compositions of the invention are suitably selected from silicone, wax, vegetable and hydrocarbon oil and phosphate ester varieties. Suitable silicone suds controlling agents include polydimethylsiloxanes having a molecular weight in the range from 200 to 200,000 and a kinematic viscosity in the range from 20 to 2,000,000 $mm^2/s$ (cSt), preferably from 3000 to 30,000 $mm^2/s$ (cSt).

Water-insoluble detergent builders can also be used. A specific example of such builders are the zeolites especially the sodium type A zeolite typified by SASIL (Registered Trade Mark). and mixtures of siloxanes and hydrophobic silanated (e.g. trimethylsilanated) silica having a particle size in the range from 10 to 20 millimicrons and a specific surface area above 50 $m^2/g$. Suitable waxes include microcrystalline waxes having a melting point in the range from 65° C. to 100° C., a molecular weight in the range from 4,000-10,000 and a penetration value of at least 6, measured at 77° C. by ASTM-D1321 and also paraffin waxes, synthetic waxes and natural waxes. Suitable phosphate esters include mono- and/or di-$C_{16}$-$C_{22}$ alkyl or alkenyl phosphate esters, and the corresponding mono- and/or di alkyl or alkenyl ether phosphates containing up to 6 ethoxy groups per molecule.

Suds suppressors are normally present in an amount from 0.01 to 5% w/w of the total composition depending upon the type of suds suppressor used, and is preferably from 0.1 to 2% w/w.

A highly preferred component of detergent compositions in accordance with the invention is one or more detergent builder salts which may comprise up to 90% of the composition, more typically from 10 to 70% by weight thereof. Suitable detergent builder salts useful herein can be of the polyvalent inorganic and polyvalent organic types or mixtures thereof. Examples of suitable water-soluble, inorganic alkaline detergent builder salts include the alkali metal carbonates, borates, phosphates, pyrophosphates, tripolyphosphates and bicarbonates.

Examples of suitable organic alkaline detergency builder salts are water-soluble polycarboxylates such as the salts of nitrilotriacetic acid, lactic acid, glycollic acid and ether derivatives thereof; succinic acid, malonic acid, (ethylenedioxy)diacetic acid, maleic acid, diglycollic acid, tartaric acid, tartronic acid and fumaric acid; citric acid, aconitic acid, citraconic acid, carboxymethyloxysuccinic acid, lactoxysuccinic acid, and 2-oxy-1,1,3propane tricarboxylic acid; oxydisuccinic acid, 1,1,2,2-ethane tetracarboxylic acid, 1,1,3,3-propane tetracarboxylic acid and 1,1,2,3-propane tetracarboxylic acid; cyclopentane cis, cis,cistetracarboxylic acid, cyclopentadiene pentacarboxylic acid, 2,3,4,5-tetrahydrofuran-cis, cis, cis-tetracarboxylic acid, 2,5-tetrahydrofuran-cis-dicarboxylic acid, 1,2,3,4,5,6-hexanehexacarboxylic acid, mellitic acid, pyromellitic acid and the phthalic acid derivatives.

Mixtures of organic and/or inorganic builders can also be used.

Chelating agents, soil suspending and anti-redeposition agents, optical brightening agents, enzymes, colours and perfumes may also be added to the detergent composition.

Chelating agents that can be incorporated include citric acid, nitrilotriacetic and ethylene diamine tetra acetic acids and their salts, organic phosphonate derivatives such as those disclosed in U.S. Pat. Nos. 3,213,030, 3,433,021, 3,292,121 and 2,599,807 and carboxylic acid builder salts such as those disclosed in U.S. Pat. No. 3,308,067. The chelating agents can be present in amounts ranging from 0.1 to 3%, suitably from 0.2 to 2% by weight of the total composition.

The detergent compositions containing the bleach activators of the present invention may contain, in addition, minor conventional additives such as fragrances perfumes and the like.

Thus the bleach activators of the present invention should find wide use in detergent compositions which use the inorganic bleach precursors. The fact that these anhydrides activate the bleach precursors at relatively lower temperatures e.g. from 20°-60° C. than those used hitherto should enable a considerable energy saving to be achieved, when the detergents are used.

The present invention is further illustrated with reference to the accompanying Examples.

EXAMPLE 1

Preliminary washing/bleaching tests were carried out on standard stained cloth swatches (EMPA* red wine 1"×4") in a beaker maintained at a constant temperature of 40° C. using the base detergent powder composition (Table 1) and the various bleach activators described in Table 2.

*The following Examples were carried out using a testing technique prescribed by the Swiss Federal testing agency, Eidenössische Material Früsungs und Versuchsanstalt Ch-9001, St Gallen Unterstrasse, PO Box 977, Switzerland. This is hereafter identified as "EMPA".

2.4 g of base detergent plus 0.45 g of sodium perborate tetrahydrate plus bleach activator (0.15 g, 5.0% w/w) as described in Table 2 were added to 600 ml of tap water at 40° C. having a hardness of about 290 ppm of calcium carbonate. Red wine stained swatches added, then the composition stirred for 30 minutes at 40° C. after which the swatches were removed, rinsed in tap water and dried at 24° C. The stain removal achieved by each bleach activator was assessed visually, using standard lighting conditions (ICS-Texicon Multilight Cabinet, D65) and compared to the stain removal achieved by TAED (10) and that of a blank run (using perborate alone, O), in which no bleach activator was used, and a rating awarded.

TABLE 1

| | % |
|---|---|
| Linear sodium alkyl benzene sulphonate (mean length of alkyl chain $C_{11.5}$) | 8.0 |
| Ethoxylated tallow alcohol (14 EO) | 2.9 |
| Sodium soap (chain length $C_{12}$-$C_{16}$: 13-26% $C_{18}$-$C_{22}$: 74-87%) | 3.5 |
| Sodium triphosphate | 43.8 |
| Sodium silicate ($SiO_2$:$Na_2O$ = 3.3:1) | 7.5 |
| Magnesium silicate | 1.9 |

TABLE 2

Visual Rating of Stain Removal
Isatoic Anhydride Derivatives
(Beaker, Red Wine Cloths, 30 Minutes, 40° C. 5% Activator)

| R | X | Method of Preparation | Visual Rating |
|---|---|---|---|
| H | H | ref 1 | 10 |
| H | 6,7-Dimethoxy | ref 2 | 10 |
| H | 8-Methyl | ref 2 | 9 |
| H | 6-Methyl | ref 2 | 9 |
| H | 5-Methyl | ref 2 | 10 |
| H | 6-Chloro | ref 2 | 9 |
| H | 7-Chloro | ref 2 | 9 |
| Methyl | H | ref 4 | 7 |
| 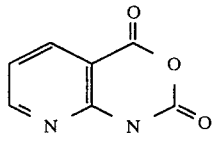 | | ref 3 | 10 |
| 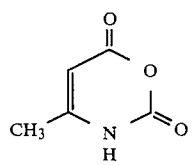 | | ref 5 | 5 |

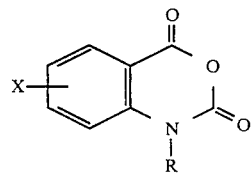

(III)

References
1. Aldrich Catalogue No. I-1,280-8, (1988-89).
2. See Synthesis below.
3. U.S. Pat. No. 3,622,573.
4. Aldrich No. 12,988-7 (1988-89).
5. J. D. Warren, J. H. MacMillan, and S. S. Washburne, J. Org. Chem., 1975, 40, 7413.

Synthesis of Bleach Activators

The respective anthranilic acid ($1 \times 10^{-2}$ mol) was dissolved with stirring in dry THF (100 ml) under nitrogen. Bis(trichloromethyl)carbonate ("triphosgene") ($1 \times 10^{-2}$ mol) was added dropwise and then the mixture heated under reflux for 15 minutes. On cooling a solid precipitated, and this was the desired activator, which was collected by filtration and dried under vacuum.

EXAMPLE 2

Further washing/bleaching tests were carried out on standard stained cloth swatches (EMPA red wine stained 2"×6") using the base detergent powder composition (Table 1) and the various bleach activators described in Table 3 in a terg-o-tometer. The terg-o-tometer was maintained at a constant temperature of 40° C. and operated at 75 rpm.

4 g of base detergent plus 0.75 g sodium perborate tetrahydrate plus bleach activator (0.25 g, 5.0% w/w) as described in Table 3 were added to one litre of tap water at 40° C., having a hardness of about 290 ppm as calcium carbonate. Red wine swatches were added, then the composition agitated for 20 minutes at 40° C. after which the swatches were removed, rinsed in tap water and dried at 24° C. The reflectance of the swatches were taken before and after using an ICS Micromatch reflectometer and the percentage stain removal (% SR) calculated by applying the following formula where L represents whiteness parameter generated by the reflectometer (black=0 and white=100).

$$\% SR = \frac{L \text{ sample} - L \text{ redwine}}{L \text{ white} - L \text{ redwine}} \times 100$$

Three replicates were run and the average result is quoted.

TABLE 3

Percentage Stain Removal
Isatoic Anhydride Derivatives
(Terg-o-Tometer, Red Wine Cloths, 20 Minutes, 40° C., 5% Activator)

| R | X | % Stain Removal |
|---|---|---|
| H | H | 76.0 |
| H | 6,7-dimethoxy | 78.5 |
| H | 8-Methyl | 75.3 |
| H | 6-Methyl | 74.2 |
| H | 5-Methyl | 79.1 |
| H | 6-Chloro | 73.8 |
| H | 7-Chloro | 76.3 |
| TAED | | 76.0 |
| Perborate | | 60.3 |

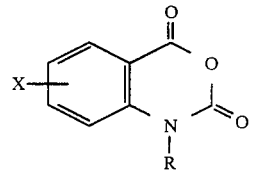

(III)

We claim:

1. A detergent composition in aqueous solution comprising
   (i) a surfactant selected from anionic, non-ionic, zwitterionic and cationic surfactants and mixtures thereof,
   (ii) a precursor compound capable of giving rise to a peroxygen compound in the presence of water,
   (iii) a bleach activator capable of enhancing the bleaching activity of the peroxygen compound so formed,
   (iv) a suds suppressing agent, and
   (v) a detergent builder, characterised in that the bleach activator comprises one or more cyclic anhydrides containing at least one nitrogen atom in the alpha position with respect to at least one of the carbonyl functions in the anhydride, and the activator is at least partially soluble in water.

2. A detergent composition according to claim 1 wherein the bleach activator has the generic formula

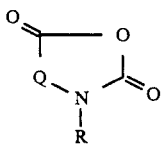

wherein Q is a divalent organic grouping such that Q and N together with the carbonyl and oxygen function in the anhydride form one or more cyclic structures, and R is a group selected from H, an alkyl, aryl, halogen, and a carboxylic or a carbonyl containing function.

3. A detergent composition according to claim 1 or 2 wherein the bleach activator has the formula

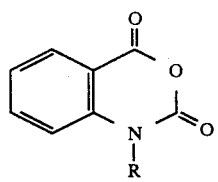

wherein R=H or an alkyl group.

4. A detergent composition according to claim 1 or 2 wherein the bleach activator has the formula

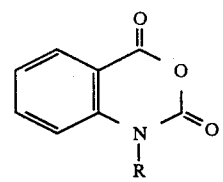

wherein R has the same significance as in claim 2 and, $R_1$, $R_2$, $R_3$ and $R_4$ may be the same or different nuclear substituents and may be selected from H halogen, alkyl, alkenyl, aryl, alkoxyl, amino, $COOR_5$ (where $R_5$ is an H or an alkyl group) and carbonyl containing groups.

5. A detergent composition according to claim 4 wherein the bleach activator is a compound of formula (III) and wherein the specific compounds have the following combination of substituents.

(a) $R=R_1=R_4=H$ and $R_2=R_3=OCH_3$
(b) $R=R_1=R_2=R_3=H$ and $R_4=CH_3$
(c) $R=R_1=R_3=R_4=H$ and $R_2=CH_3$
(d) $R=R_2=R_3=R_4=H$ and $R_1=CH_3$
(e) $R=R_1=R_3=R_4=H$ and $R_2=Cl$ or $Br$
(f) $R=R_1=R_2=R_4=H$ and $R_3=Cl$ or $CO_2H$ or $NO_2$, or
(g) $R_1=R_2=R_3=R_4=H$ and $R=CH_3CO$. or $Cl$ 6. A detergent composition according to claim 1 or 2 wherein the bleach activator has the formula

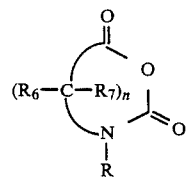

wherein R has the same significance as in claim 2 and $R_6$ and $R_7$ are the same or different groups described in respect of $R_1$ to $R_4$ in claim 4 and n has a value from 1 to 3.

7. A detergent composition according to claim 1 or 2 wherein the bleach activator has the formula (V)

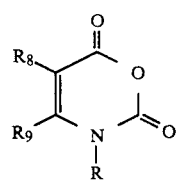

wherein R has the same significance as in claim 2, and $R_8$ and $R_9$ are the same or different groups denoted by the substituents $R_1$–$R_4$ in claim 4, or, which together form one or more cyclic structures with or without additional hetero atoms.

8. A detergent composition according to claim 1 or 2 wherein the surfactant (i) is present in an amount from 1 to 70% w/w of the total composition.

9. A detergent composition according to claim 1 or 2 wherein the precursor compound (ii) acts as a source of hydrogen peroxide.

10. A detergent composition according to claim 9 wherein the precursor compound (ii) is selected from sodium perborate mono or tetra-hydrate, sodium percarbonate, sodium persilicate, and the clathrate $4Na_2.SO_4:2H_2O_2:NaCl$.

11. A detergent composition according to claim 9 wherein the precursor compound acting as hydrogen peroxide source is present in an amount from 1–40% w/w of the total composition.

12. A detergent composition according to claim 10, wherein the molar ratio of the hydrogen peroxide generated by the precursor compound (ii) to the bleach activator (iii) is greater than 1.5:1.

13. A detergent composition according to claim 1 or 2 wherein the amount of suds suppressing agents (iv) range from 0.01 to 5% w/w of the total composition.

14. A detergent formulation according to claim 1 or 2, wherein the detergent builder (v) is a salt and comprises up to 90% w/w of the total composition.

* * * * *